(12) United States Patent
Ehr et al.

(10) Patent No.: US 6,685,653 B2
(45) Date of Patent: Feb. 3, 2004

(54) EXTENSION SYSTEM FOR PRESSURE-SENSING GUIDEWIRES

(75) Inventors: Timothy G.J. Ehr, Elk River, MN (US); Bruce Howard Asmus, Minnetonka, MN (US); James E. Mayberry, Champlin, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 14 days.

(21) Appl. No.: 10/024,948

(22) Filed: Dec. 19, 2001

(65) Prior Publication Data

US 2003/0114775 A1 Jun. 19, 2003

(51) Int. Cl.⁷ .......................... A61B 5/00; A61M 25/00
(52) U.S. Cl. .................................................. 600/585
(58) Field of Search ........................... 600/585, 434, 600/486, 561; 604/154, 164.13, 523

(56) References Cited

U.S. PATENT DOCUMENTS

| | | | |
|---|---|---|---|
| 4,827,941 A | 5/1989 | Taylor et al. ............... 128/657 |
| 4,846,193 A | 7/1989 | Tremulis et al. ............ 128/772 |
| 4,875,489 A | 10/1989 | Messner et al. ............ 128/772 |
| 4,922,923 A | 5/1990 | Gambale et al. ............ 128/772 |
| 4,964,409 A | * 10/1990 | Tremulis .................... 600/434 |
| 4,966,136 A | 10/1990 | Bates ........................ 128/87 R |
| 5,050,606 A | 9/1991 | Tremulis .................... 128/637 |
| 5,113,872 A | 5/1992 | Jahrmarkt et al. .......... 128/772 |
| 5,117,838 A | 6/1992 | Palmer et al. .............. 128/772 |
| 5,246,009 A | 9/1993 | Adams ....................... 128/772 |
| 5,247,942 A | 9/1993 | Prather et al. .............. 128/772 |
| 5,271,415 A | 12/1993 | Foerster et al. ............ 128/772 |
| 5,546,958 A | 8/1996 | Thorud et al. .............. 128/772 |
| 5,651,373 A | 7/1997 | Mah .......................... 128/772 |
| 5,666,968 A | 9/1997 | Imran et al. ................ 128/772 |
| 5,701,911 A | 12/1997 | Sasamine et al. ........... 128/772 |
| 5,788,653 A | 8/1998 | Lorenzo ..................... 600/585 |
| 5,813,405 A | 9/1998 | Montano, Jr. et al. |
| 5,813,996 A | 9/1998 | St. Germain et al. ....... 600/585 |
| 5,853,375 A | 12/1998 | Orr ............................ 600/585 |
| 5,853,385 A | 12/1998 | Emerich et al. |
| 5,860,938 A | 1/1999 | Lafontaine et al. |
| 6,080,117 A | 6/2000 | Cornelius ................... 600/585 |
| 6,193,706 B1 | 2/2001 | Thorud et al. .............. 604/533 |

FOREIGN PATENT DOCUMENTS

EP 0815892 A1 7/1998

OTHER PUBLICATIONS

International Search Report dated Jun. 4, 2003 (8 pages).

* cited by examiner

Primary Examiner—Max F. Hindenburg
Assistant Examiner—Brian Szmal
(74) Attorney, Agent, or Firm—Marshall, Gerstein & Borun LLP

(57) ABSTRACT

An extension system for a pressure-sensing guidewire is disclosed. The guidewire includes an elongated tubular member having a proximal end, a distal end and a lumen extending between the proximal and distal ends. The guidewire also includes at least one opening disposed adjacent the distal end of the tubular member for providing fluid communication to the lumen. The system also includes an elongated extension member that is detachably connected to the proximal end of the tubular member. The system enables a catheter to be inserted over a pressure-sensing guidewire without removing the pressure-sensing guidewire from a patient.

23 Claims, 2 Drawing Sheets

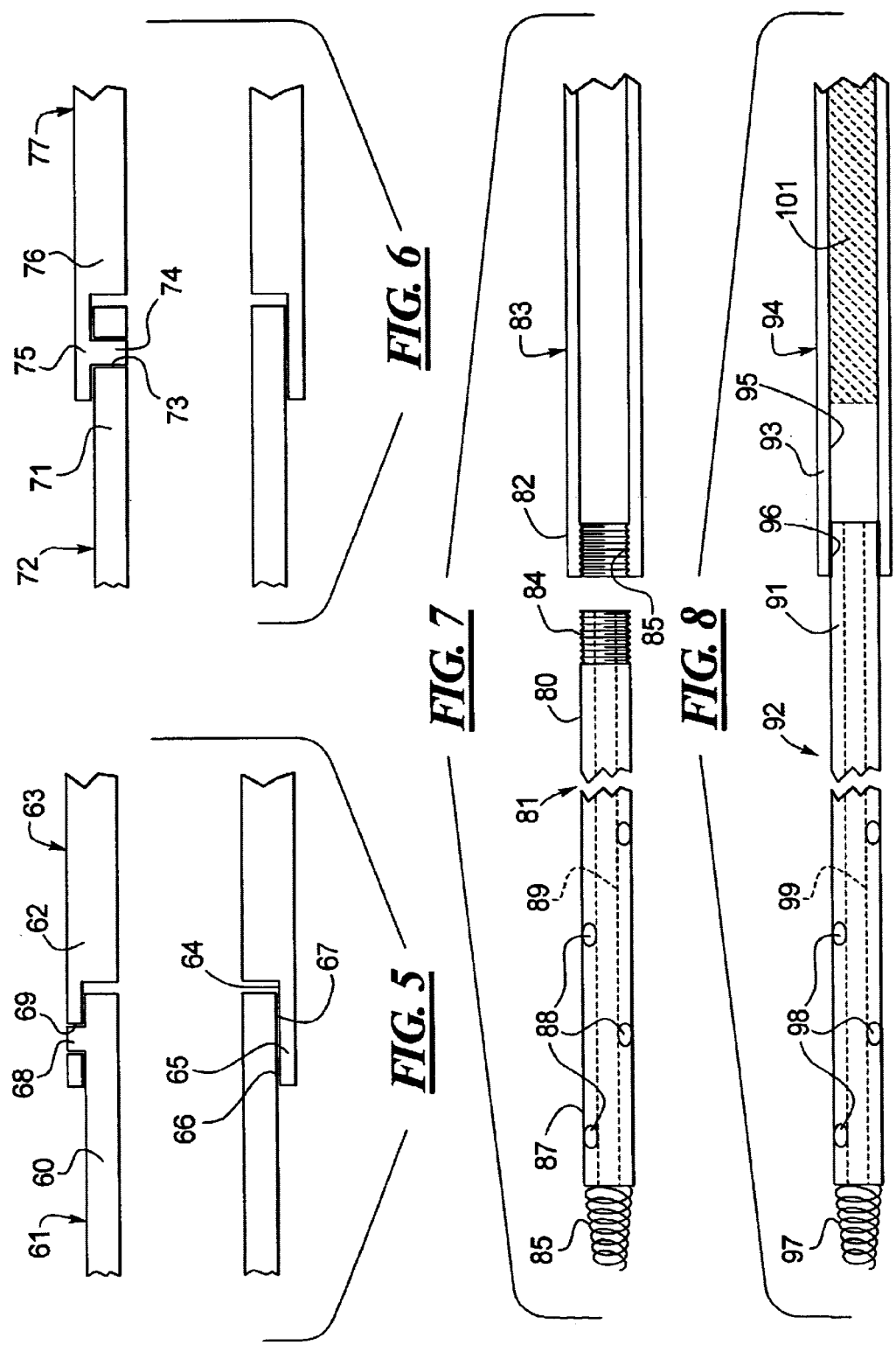

EXTENSION SYSTEM FOR PRESSURE-SENSING GUIDEWIRES

FIELD OF THE INVENTION

The present invention relates generally to the field of guidewires and, more specifically, to the field of pressure-sensing guidewires used in intravascular procedures. Still more specifically, the present invention relates to a system and method for extending the length of pressure-sensing guidewires during intravascular procedures.

BACKGROUND OF THE INVENTION

Guidewires are used in various medical procedures to position medical devices at desired locations within a patient's vascular system. Guidewires are inserted into the patient's vasculature and steered or maneuvered within a guide catheter to a location of interest. Once in place, the guidewire provides the means to place a device, such as a catheter, within the patient's vasculature at the location of interest.

Pressure-sensing guidewires are also utilized for medical procedures. Typically, pressure-sensing guidewires comprise a hollow wire with at least one opening disposed towards the distal end of the wire. Pressure is communicated through the opening and down the lumen defined by the wire to the proximal end of the wire. The proximal end of the wire is then connected to a transducer for measuring the intravascular pressure communicated through the guidewire. Knowledge of the intravascular pressure at specific locations within a vessel or artery is important in determining whether angioplasty should be performed at all.

In angioplasty a dilatation catheter having an inflatable balloon structure is used to compress an occlusion or stenosis against the sides of a vessel, thereby permitting circulation to be reestablished. After the location of the occlusion is identified, a pressure-sensing guidewire is inserted into the patient's artery and maneuvered or steered to the location of the restriction. Maneuvering of the guidewire is facilitated by fluoroscopy which allows the physician to observe the movement of the guidewire. The guidewire generally comprises a radiopaque material to enhance viewing. Preferably, vascular pressure both proximal and distal to the occlusion is measured to determine if treatment is necessary.

If angioplasty is to be performed, a dilatation catheter is inserted over the guidewire so that its working segment is located adjacent the occlusion. During an angioplasty procedure, the dilatation catheter balloon is inflated to open the restriction, and then is subsequently removed along with the guidewire. However, instances sometimes arise which prevent the physician from completing the procedure. Sometimes a different size balloon is required further to dilate the vascular occlusion, or another device or other type of catheter is needed to remove plaque material. A guidewire extension system is needed when the catheter, or other such device, has to be removed and replaced with another device or catheter.

In the usual procedure to exchange catheters, the guidewire is removed from the patient, leaving the catheter in the vascular system. An exchange wire is inserted through the catheter and the catheter is removed, leaving the exchange wire in place. The new catheter is inserted over the exchange wire and the exchange wire removed and replaced with the guidewire.

It is desirable to keep the guidewire in the patient's vasculature instead of withdrawing the guidewire as described above and replacing it with a longer guidewire for various reasons. One reason is that the initial placement of the guidewire requires extensive, time consuming, manipulation. Removal and repositioning of the guidewire is equally time consuming. It is also important that once the guidewire has been steered to a position across an occlusion, that the position not be lost by removal of the guidewire. Guidewires that are removed from a crossed occlusion may induce spontaneous restriction or closure making repositioning of the guidewire difficult.

In those cases where a catheter exchange is required, it is desirable to remove the catheter over the guidewire, leaving the guidewire positioned in the patient. However, to permit a catheter exchange, a guidewire over which a catheter is to be exchanged must be long enough to allow the physician to grip a portion of the wire as the catheter is being withdrawn over the guidewire. This requires the guidewire to be long enough to provide an external portion beyond the catheter in addition to the guidewire portion remaining in the patient. Typically, the guidewire must be 110–180 cm longer than the catheter in order for an exchange to be executed.

However, guidewires, and, more specifically, hollow pressure-sensing guidewires that are too long have inferior handling characteristics, thereby making it more difficult to steer and maneuver the guidewire. The added length needed for an exchange also causes the proximal end of the guidewire to be exposed from the patient and possibly being non-sterile and difficult for the physician to maneuver in the procedure. It is for these reasons that guidewires are typically only slightly longer than balloon catheters, e.g., 20–50 centimeters longer, and that a much longer exchange wire is used only with exchange procedures.

A dilatation catheter has a shaft length in the range of about 120 cm to about 150 cm. A suitable guidewire for such a catheter would have a length in the range of about 150 cm to about 180 cm and a suitable exchange guidewire would have a length in the range of about 260 cm to about 330 cm. As can be imagined from the above, utilization of an exchange guidewire in a catheter exchange procedure is complicated and time consuming.

Coupling or connecting a second length of wire, sometimes called an extension wire or secondary wire, to the exposed, proximal end of a positioned guidewire is known. The secondary wire length should be sufficient to allow the catheter to be withdrawn while leaving the primary guidewire positioned within the patient's coronary or peripheral vasculature. Various approaches have been suggested for effecting the attachment of an extension wire to a guidewire.

The prior art guidewire extension systems all have one or more drawbacks. Some are difficult or tedious or intricate to engage and disengage. Others simply do not disengage. While frictional engagement overcomes the disadvantages of crimping, disengagement may occur too easily. Some connector systems are difficult or expensive to build, especially in smaller diameter sizes.

Further, none of the above-described guidewire extension systems are designed to be used with pressure-sensing guidewires. That is, none of the extension systems described above are designed to be used with a hollow pressure-sensing guidewire. They are all intended to be used and designed for a solid guidewire structure.

Because of the emergence of pressure-sensing guidewires and the importance of measuring vascular pressure at points both proximal and distal to an occlusion prior to the performance of angioplasty procedure, an improved extension system for pressure-sensing guidewires is desired.

SUMMARY OF THE INVENTION

The present invention overcomes the deficiencies of the prior art by providing a pressure-sensing guidewire assembly that includes an extension member. The guidewire assembly comprises a pressure-sensing guidewire comprising an elongated tubular member comprising a proximal end, a distal end and a lumen extending between the proximal and distal ends. The guidewire further comprises at least one opening disposed adjacent the distal end for providing fluid communication to the lumen. The assembly further comprises an elongated extension member detachably connected to the proximal end of the elongated tubular member.

In another embodiment, a method for extending the length of a pressure-sensing guidewire is provided wherein the guidewire comprises an elongated tubular member comprising a proximal end, a distal end and a lumen extending between the proximal and distal ends. The guidewire further comprises at least one opening disposed adjacent the distal end for providing fluid communication to the lumen. The method comprises the step of connecting an elongated extension member to the proximal end of the tubular member.

BRIEF DESCRIPTION OF THE DRAWINGS

FIG. 5 is a partial sectional view of a proximal end of a pressure-sensing guidewire connected to an extension member using a key/slot connection and/or a male/female frictional connection.

FIG. 6 is a partial sectional view of a proximal end of a pressure-sensing guidewire connected to an extension member using a key/slot connection and/or a male/female frictional connection.

FIG. 7 is a partial sectional view illustrating a pressure-sensing guidewire and extension member that can be threadably connected together.

FIG. 8 is a partial sectional view of a pressure-sensing guidewire and extension member connected with a male/female frictional connection.

DETAILED DESCRIPTION OF THE PRESENTLY PREFERRED EMBODIMENT

Figure 1:
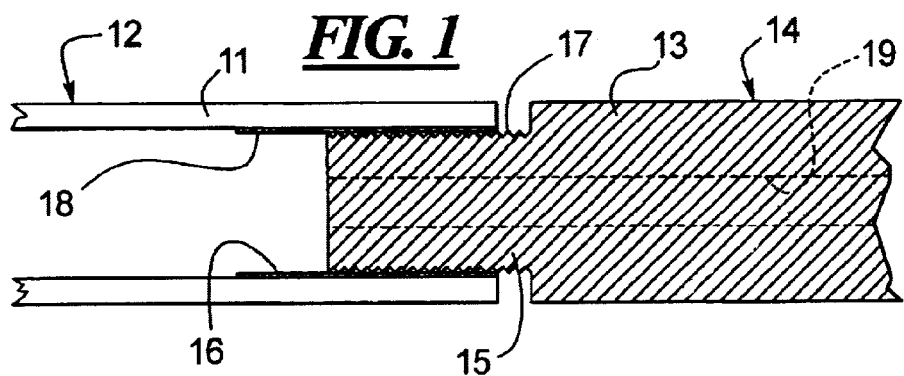
FIG. 1 is a partial sectional view of a proximal end of a pressure-sensing guidewire and a distal end of an extension member.

Turning to FIG. 1., a proximal end 11 of a pressure-sensing guidewire 12 is illustrated as it is being connected to a distal end 13 of an extension member 14. The distal end 13 includes a male member 15 that is frictionally received within a female hole or opening 16 of the proximal end 11 of the pressure-sensing guidewire 12. The male member 15 may include a plurality of grooves or ridges 17 and the opening 16 of the guidewire 12 may also include a roughened surface 18 to enhance the frictional connection between the male member 15 and opening 16. The extension member 14 may be either solid or tubular with a lumen 19 extending therethrough for communication of the fluid pressure.

Figure 2:
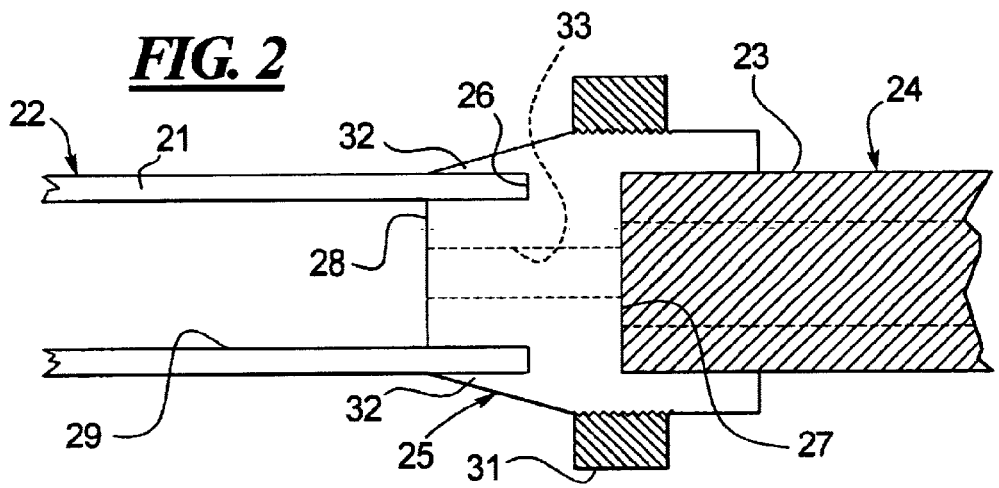
FIG. 2 is a partial sectional view of a proximal end of a pressure-sensing guidewire being connected to a distal end of an extension member by way of a collet and compression collar.

FIG. 2 illustrates a proximal end 21 of a pressure-sensing guidewire 22 being connected to a distal end 23 of an extension member 24 by way of a collet 25. The collet 25 includes two open ends 26, 27. In the embodiment shown in FIG. 2, the open end 26 of the collet 25 is annulus-shaped for receiving the proximal end 21 of the hollow pressure-sensing guidewire 22. The member 28 is received within the opening 29 of the guidewire 22. However, the opening 26 may also be fashioned similar to the opening 27 which, as shown in FIG. 2, receives the distal end 23 of the extension member 24. It is anticipated that the distal end 23 of the extension member 24 will most likely be permanently connected to the collet 25 and that the compression collar 31 would be utilized to secure the guidewire 22 to the collet 25. That is, rotating the compression collar 31 onto the collet 25 will result in one or more fingers shown at 32 extending radially inwardly to clamp down onto the guidewire 22. The collet 25 may also include a lumen 33 and the extension member 24 may also include a lumen 34 for the communication of fluid pressure.

Figure 3:
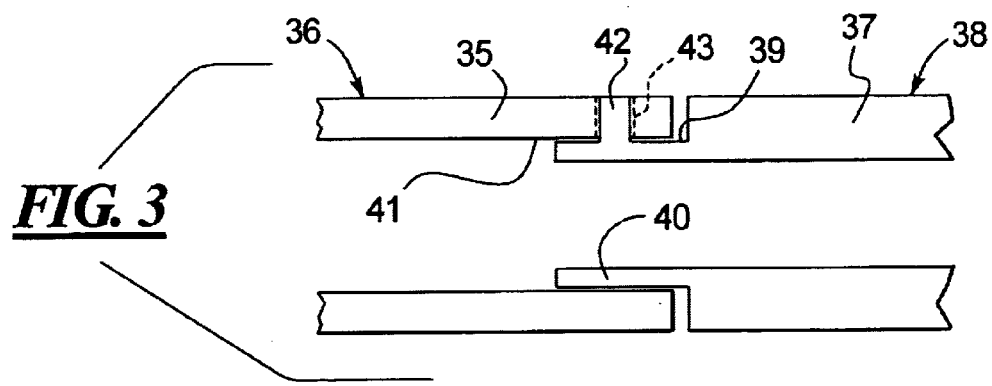
FIG. 3 is a partial sectional view of a proximal end of a pressure-sensing guidewire connected to an extension member using a key/slot connection and/or a male/female frictional connection.

In FIG. 3, another male/female connection is illustrated between the proximal end 35 of a guidewire 36 and the proximal end 37 of an extension member 38. The proximal end 37 of the extension member 38 includes a cut out portion 39 and an inwardly extending ledge 40 which can be frictionally received in the opening 41 of the guidewire 36. A frictional engagement between the ledge 40 and the opening 41 is often sufficient to provide a sealed and sufficiently strong connection. However, the ledge 40 may also be equipped with a protuberance or key 42 which may be received in a hole or slot 43 disposed in the proximal end 35 of the guidewire 36.

Figure 4:
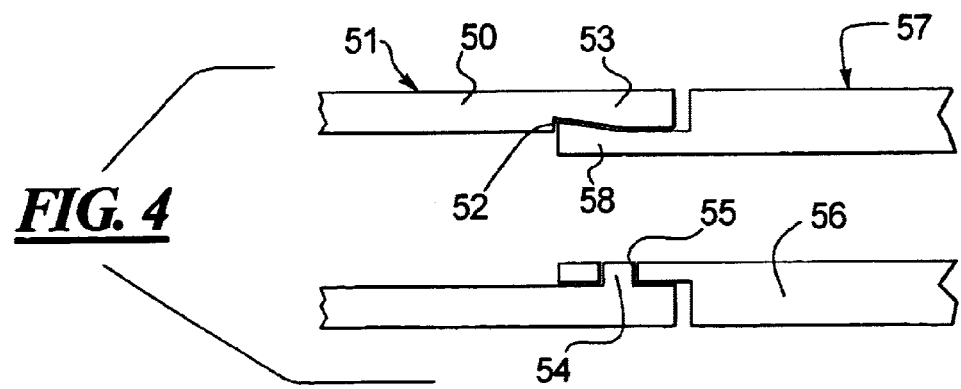
FIG. 4 is a partial sectional view of a proximal end of a pressure-sensing guidewire connected to an extension member using a key/slot connection and/or a male/female frictional connection.

Turning to FIG. 4, the proximal end 50 of the guidewire 51 includes a stepped or cut out portion 52. The resulting ledge 53 includes a radially inwardly extending key or protuberance 54. This key or protuberance 54 is received in a hole or slot 55 disposed in the proximal end 56 of the extension member 57. Again, the key 54/slot 55 connection is optional. It is anticipated that a secure frictional connection can be achieved by engagement of the mating ledges 53, 58 with or without grooves, serrations or other frictional enhancements.

Turning to FIG. 5, the proximal end 60 of the pressure-sensing guidewire 61 serves as the male connection member and the proximal end 62 of the extension member 63 serves as the female counterpart. In the embodiment shown in FIG. 5, the proximal end 62 of the extension member 63 includes a cut out portion 64 resulting in a ledge 65. Again, a frictional connection can be achieved between the inner surface 66 of the ledge 65 and the outer surface 67 of the guidewire 61. However, to create a more secure connection, the proximal end 60 of the guidewire 61 can be equipped with a radially outwardly extending key or protuberance 68 that can be received in a hole or slot 69 disposed in the ledge 65 of the extension member 63.

Similarly, in FIG. 6, the proximal end 71 of the guidewire 72 includes a hole or slot 73 which receives a radially inwardly extending protuberance or key 74 that extends inward from the ledge 75 the distal end 76 of the extension member 77. Again, the key/slot connection is not required, it is anticipated that a frictional connection will suffice.

Turning to FIGS. 7 and 8, FIG. 7 illustrates a threaded connection between a proximal end 80 of a pressure-sensing guidewire 81 and a distal end 82 of an extension member 83. In the embodiment shown in FIG. 7, the proximal end 80 of the guidewire 81 includes threads 84 and is received in the threaded opening 85 of the extension member 83. An atraumatic spring tip 86 is shown at the distal end 87 of the guidewire 81. One or more holes or openings 88 are also provided to provide communication between the vascular environment and the lumen 89 of the guidewire 81. In FIG. 8, a similar embodiment is shown with a frictional male/female connection. Again, the proximal end 91 of a pressure-sensing guidewire 92 is received in the distal end 93 of an extension member 94. The surfaces 95 of the extension member 94 and 96 of the guidewire 92 may include ridges or other frictional enhancements. An atraumatic tip is shown at 97 and holes or openings are shown at 98 for providing communication between the vascular environment and the lumen 99. The extension member 94 may be tubular or may include a solid core 101 for the prevention of back bleeding.

The extension member may be fabricated from a variety of materials including metals, metallic alloys and various polymers. Suitable materials may include polymers such as Pebax™, Arnitel™, polybutylene terephthalente (PBT), polyoxymethylene (POM), polyethylene (PE), polyethylene terephthalate (PET), polytetrafluoroethylene (PTFE), polyvinyl chloride (PVC), thermoplastic elastomer (TPE), polyamide and Nylon™ and metallic alloys such as Inconel 617™, Inconel 625™, Hastelloy S™, Hastelloy X™, Nimonic 90™, Incoloy 800™, MP35-N Elgiloy™, 304LV™, 316 LVM™, Aermet 100™, Aermet 310™, CRB-7™, Custom 450™, Custom 455™, Custom 465m™, NiMark 250™, NiMark 250 NCO™, NiMark 300™, Nickel 200™, 304LV™, 316 LVM™, 321™, 347™, Aermet 100™, Aermet 310T™, Haynes 214™, Haynes 230™, Inconel 600™, Inconel 601™, Inconel 617™, Inconel 625™, RA 333™, Hastelloy B™, Hastelloy N™, Hastelloy S™, Hastelloy W™, Hastelloy X™, Hastelloy C-276™, Haynes HR-120™, Haynes HR-160™, Nimonic 75™, Nimonic 86™, Haynes 556™, Incoloy 800™, Incoloy 800H™, Incoloy 800HT™, Incoloy 801™, Incoloy 802™, MP35-N™ and Elgiloy™, as well as other suitable materials not listed here but that will be apparent to those skilled in the art.

While the specification describes preferred designs and methods, those skilled in the art will appreciate the spirit and scope of the invention with reference to the appended claims.

What is claimed:

1. A pressure sensing guidewire assembly comprising:
   a pressure sensing guidewire comprising an elongated tubular member comprising a proximal end, a distal end, a lumen extending between the proximal and distal ends, and at least one opening disposed adjacent the distal end for providing fluid communication to the lumen,
   an elongated extension member having a tubular distal end detachably connected to the proximal end of the tubular member thereby permitting separation of the extension member from the guidewire.

2. The pressure sensing guidewire assembly of claim 1 wherein the proximal end of the tubular member comprises a female opening and the tubular distal end of the extension member is received in the female opening of the proximal end of the tubular member.

3. The pressure sensing guidewire assembly of claim 2 wherein the tubular distal end of the extension member frictionally engages the female opening of the proximal end of the tubular member.

4. The pressure sensing guidewire assembly of claim 2 wherein the tubular distal end of the extension member threadably engages the female opening of the proximal end of the tubular member.

5. The pressure sensing guidewire assembly of claim 2 wherein the tubular distal end of the extension member comprises a radially outwardly extending protuberance and the proximal end of the tubular member comprises a hole or slot that receives the protuberance of the extension member.

6. The pressure sensing guidewire assembly of claim 2 wherein the tubular distal end of the extension member comprises a hole or slot and the proximal end of the tubular member comprises a radially inwardly extending protuberance that is received in the hole or slot of the extension member.

7. The pressure sensing guidewire assembly of claim 2 wherein portions of the extension member proximal to the tubular distal end are also tubular.

8. The pressure sensing guidewire assembly of claim 2 wherein at least part of the extension member is solid.

9. The pressure sensing guidewire assembly of claim 1 wherein the proximal end of the tubular member comprises a female opening and the extension member is particularly solid and the tubular distal end of the extension member mateably engages the female opening of the proximal end of the tubular member.

10. The pressure sensing guidewire assembly of claim 9 wherein the tubular distal end of the extension member frictionally engages the female opening of the proximal end of the tubular member.

11. The pressure sensing guidewire assembly of claim 9 wherein the tubular distal end of the extension member threadably engages the female opening of the proximal end of the tubular member.

12. The pressure sensing guidewire assembly of claim 9 wherein the tubular distal end of the extension member comprises a radially outwardly extending protuberance and the proximal end of the tubular member comprises a hole or slot that receives the protuberance of the extension member.

13. The pressure sensing guidewire assembly of claim 9 wherein the tubular distal end of the extension member comprises a hole or slot and the proximal end of the tubular member comprises a radially inwardly extending protuberance that is received in the hole or slot of the extension member.

14. A pressure sensing guidewire assembly comprising:
   a pressure sensing guidewire comprising an elongated tubular member comprising a proximal end, a distal end, a lumen extending between the proximal and distal ends, and at least one opening disposed adjacent the distal end for providing fluid communication to the lumen,
   an elongated extension member detachably connected to the proximal end of the tubular member,
   a collet comprising a body having two opposing open ends, the proximal end of the tubular member being received in one of the open ends of the collet, the extension member comprising a distal end that is received in the other of the open ends of the collet,
   the body of the collet being threadably received in a compression collar.

15. The pressure sensing guidewire of claim 14 wherein the collet and extension member each have a lumen for the communication of fluid pressure therethrough.

16. A pressure sensing guidewire assembly comprising:
a pressure sensing guidewire comprising an elongated tubular member comprising a proximal end, a distal end, a lumen extending between the proximal and distal ends, and at least one opening disposed adjacent the distal end for providing fluid communication to the lumen,
an elongated extension member detachably connected to the proximal end of the tubular member,
the tubular distal end that of the extension member comprises a female opening, the proximal end of the tubular member being received in the female opening of the distal end of the extension member.

17. The pressure sensing guidewire assembly of claim 16 wherein the female opening of distal end of the extension member frictionally engages the proximal end of the tubular member.

18. The pressure sensing guidewire assembly of claim 16 wherein the female opening of the distal end of the extension member threadably engages the proximal end of the tubular member.

19. The pressure sensing guidewire assembly of claim 16 wherein the female opening of the distal end of the extension member comprises a radially inwardly extending protuberance and the proximal end of the tubular member comprises a hole or slot that receives the protuberance of the extension member.

20. The pressure sensing guidewire assembly of claim 16 wherein the distal end of the extension member comprises a hole or slot and the proximal end of the tubular member comprises a radially outwardly extending protuberance that is received in the hole or slot of the extension member.

21. A pressure sensing guidewire assembly comprising:
a pressure sensing guidewire comprising an elongated tubular member comprising a proximal end, a distal end, a lumen extending between the proximal and distal ends, and at least one opening disposed adjacent the distal end for providing fluid communication to the lumen, the proximal end of the tubular member comprising a female opening, an elongated extension member detachably connected to the proximal end of the tubular member, and the extension member being solid except for a tubular male distal end that engages the female opening of the proximal end of the tubular member,
the tubular male distal end of the extension member comprising a plurality of grooves for frictionally engaging the female opening of the proximal end of the tubular member.

22. A method for extending a length of a pressure sensing guidewire comprising an elongated tubular member comprising a proximal end, a distal end, a lumen extending between the proximal and distal ends, and at least one opening disposed adjacent the distal end for providing fluid communication to the lumen, the method comprising:
detachably connecting a tubular distal end of an elongated extension member to the proximal end of the tubular member.

23. A method of preventing back bleeding through a pressure sensing guidewire that comprises an elongated tubular member comprising a proximal end, a distal end, a lumen extending between the proximal and distal ends, and at least one opening disposed adjacent the distal end for providing fluid communication to the lumen, the method comprising:
detachably connecting a tubular distal end of an otherwise solid extension member to the proximal end of the tubular member to sealably engage the proximal end of the tubular member and prevent back bleeding therethrough, the extension member being separable from the tubular member.

* * * * *

UNITED STATES PATENT AND TRADEMARK OFFICE
CERTIFICATE OF CORRECTION

PATENT NO. : 6,685,653 B2
DATED : February 3, 2004
INVENTOR(S) : Ehr et al.

It is certified that error appears in the above-identified patent and that said Letters Patent is hereby corrected as shown below:

Column 7,
Line 10, after "distal end that" please delete "end that of the extension member" and insert -- end of the extension member -- in its place.

Signed and Sealed this

Twenty-seventh Day of April, 2004

JON W. DUDAS
*Acting Director of the United States Patent and Trademark Office*